US008586796B2

(12) United States Patent
Burkhardt et al.

(10) Patent No.: US 8,586,796 B2
(45) Date of Patent: Nov. 19, 2013

(54) PROCESS TO PURIFY DIALKYL SULFIDES

(75) Inventors: Elizabeth Burkhardt, Bridgeville, PA (US); Kevin Neigh, Butler, PA (US)

(73) Assignee: BASF SE, Ludwigshafen (DE)

( * ) Notice: Subject to any disclaimer, the term of this patent is extended or adjusted under 35 U.S.C. 154(b) by 311 days.

(21) Appl. No.: 13/003,587

(22) PCT Filed: Jul. 10, 2009

(86) PCT No.: PCT/EP2009/058848
§ 371 (c)(1),
(2), (4) Date: Jan. 11, 2011

(87) PCT Pub. No.: WO2010/007006
PCT Pub. Date: Jan. 21, 2010

(65) Prior Publication Data
US 2011/0124920 A1    May 26, 2011

Related U.S. Application Data

(60) Provisional application No. 61/080,868, filed on Jul. 15, 2008.

(51) Int. Cl.
*C07F 5/02*       (2006.01)
*C07C 319/00*   (2006.01)

(52) U.S. Cl.
USPC .................................. 568/6; 568/59; 568/60

(58) Field of Classification Search
USPC ................................................ 568/6, 59, 60
See application file for complete search history.

(56) References Cited

U.S. PATENT DOCUMENTS

| | | | |
|---|---|---|---|
| 4,173,619 A | 11/1979 | Erickson |
| 4,358,297 A | 11/1982 | Eberly, Jr. |
| 4,964,957 A | 10/1990 | Shaw et al. |
| 4,999,175 A | 3/1991 | Vansant et al. |
| 5,157,201 A | 10/1992 | Norris |
| 5,302,771 A | 4/1994 | Venkatram et al. |
| 5,382,417 A | 1/1995 | Haase |
| 5,433,828 A | 7/1995 | van Velzen et al. |
| 5,439,641 A | 8/1995 | Caupin et al. |
| 5,480,860 A | 1/1996 | Dillon |
| 5,559,271 A | 9/1996 | Shaw et al. |
| 6,015,536 A | 1/2000 | Lokkesmoe et al. |
| 6,124,410 A | 9/2000 | Ito et al. |
| 6,136,144 A | 10/2000 | Martin et al. |
| 6,277,344 B1 | 8/2001 | Hei et al. |
| 6,436,174 B1 | 8/2002 | Grossmann et al. |
| 6,639,110 B2 | 10/2003 | Fremy |
| 6,736,879 B2 | 5/2004 | Hasenberg et al. |
| 2003/0205134 A1 | 11/2003 | Hasenberg et al. |
| 2005/0205470 A1 | 9/2005 | Ramirez-Corredores et al. |

FOREIGN PATENT DOCUMENTS

DE    19828977 A1    12/1999
JP    49006287       2/1974

OTHER PUBLICATIONS

Carey, et al., "Analysis of the reactions used for the preparation of drug candidate molecules," *Organic & Biomolecular Chemistry* (2006), pp. 2337-2347.
Corey, et al., "Reduction of Carbonyl Compounds with Chiral Oxazaborolidine Catalysts: A New Paradigm for Enantioselective Catalysis and a Powerful New Synthetic Method," *Angew. Chem. Int. Ed.* (1998), vol. 37, pp. 1986-2012.
Coyle, et al., "Molecular Addition Compounds of Boron. II. Thiopane-Borane and Related Adducts," *Journal of the American Chemical Society* (1959), pp. 2989-2994.
Dunn, et al., *Carbon Disulphide in Organic Chemistry* (1998), p. 316.
Kotter et al. DW00740069223V (1974).
Rowe, "Aroma Chemicals for Savory Flavors," *Perfumer & Flavorist* (Jul./Aug. 1998), vol. 23, pp. 9-16.
Roy, "Thiols and Organic Sulfides," *Ullman's Encyclopedia of Industrial Chemistry*, vol. 36, (1998) pp. 625-652.
Stepanenko, et al., "Highly enantioselective carbonyl reduction with borane catalyzed by chiral spiroborate esters derived from chiral 1,2-aminoalcohols," *Tetrahedron: Asymmetry* (2006), vol. 17, pp. 112-115.
Xavier, et al., "(S)-Tetrahydro-1-Methyl-3,3-Diphenyl-1H,3H-Pyrrolo-[1,2-c][1,3,2]Oxazaborole-Borane Complex," *Organic Synthesis, Coll.* (1998), vol. 9, p. 676; (1997), vol. 74, p. 50.
Aldrich Advanced Science (2006) XP002548318.
International Preliminary Report on Patentability for the PCT counterpart application (PCT/EP2009/058848) mailed Jan. 27, 2011.

*Primary Examiner* — Jafar Parsa

(74) *Attorney, Agent, or Firm* — Novak Druce Connolly Bove + Quigg LLP

(57) ABSTRACT

The invention relates to new processes to prepare low odor dialkyl sulfides, the low odor dialkyl sulfides obtainable by these processes and to methods of using these low odor dialkyl sulfides. Moreover, the invention relates to a process to prepare dialkyl sulfide borane complexes of high purity, the dialkyl sulfide borane complexes obtainable by this process and to a process for enantioselective reductions employing these dialkyl sulfide borane complexes of high purity as reducing agent.

9 Claims, No Drawings

PROCESS TO PURIFY DIALKYL SULFIDES

CROSS-REFERENCE TO RELATED APPLICATIONS

This application is a national stage application (under 35 U.S.C. §371) of PCT/EP2009/058848, filed Jul. 10, 2009, which claims benefit of U.S. application 61/080,868, filed Jul. 15, 2008.

FIELD OF THE INVENTION

The invention relates to new processes to purify dialkyl sulfides, the purified dialkyl sulfides obtainable by these processes and to methods of using these purified dialkyl sulfides. Moreover, the invention relates to a process to prepare dialkyl sulfide borane complexes of high purity, the dialkyl sulfide borane complexes obtainable by this process and to a process for enantioselective reductions employing these dialkyl sulfide borane complexes of high purity as reducing agent.

BACKGROUND OF THE INVENTION

Dialkyl sulfides are versatile reagents for organic syntheses. Moreover, lower dialkyl sulfides are often employed as valuable solvents. Most organic sulfides with low molecular mass have intense unpleasant odors, which in many cases is further deteriorated through the presence of sulfur-containing impurities (K.-M. Roy, "Thiols and Organic Sulfides", Ullmann's Encyclopedia of Industrial Chemistry, $7^{th}$ Ed., pages 1 to 28, Wiley-VCH Verlag GmbH & Co. KGaA 2008). For example, commercial dimethyl sulfide (DMS) contains highly malodorous impurities such as carbon disulfide, carbonyl sulfide, methyl thiol, dimethyldisulfide, hydrogen sulfide and other sulfurous compounds at low levels. Even though the concentration of these impurities is less than one percent and for some compounds is less than 200 ppm, the odor of the impurities gives the DMS a vile stench of rotten eggs, cabbage and skunk. Some sulfur compounds having the odor of garlic or onions may also contribute to the odor. DMS of high purity has the odor of corn or a grassy meadow (D. J. Rowe, Perfumer & Flavorist 1998, Vol. 23, pages 9 to 14).

DMS is used as an anti-coking agent in petroleum steam-crackers and as raw material to make the solvent dimethylsulfoxide (DMSO). DMS is also used as a solvent and for coordination to metal compounds or other Lewis acids, i.e. borane compounds. Dimethyl sulfide borane (DMSB) is a stable concentrated (10M) form of borane ($BH_3$) utilized in the pharmaceutical industry for the reduction of carbonyl compounds, imines, and hydroboration of double bonds in alkenes or alkynes. The unpleasant odor of DMSB made from impure DMS can be noticed at very low levels in production operations and can drift in the wind into communities. Responsible companies do not want to subject employees or neighboring populations to the odor from using DMS or DMSB.

The purification of DMS has been addressed in JP 49006287 by a steam distillation process and separation of water from the dialkyl sulfide. This method is inappropriate for DMSB preparation due to residual water in the DMS.

U.S. Pat. No. 6,736,879 discloses an absorption method to remove carbon disulfide from dimethyl sulfide. The absorption media is an activated alumina treated with alkali metal and alkaline earth compounds and can be regenerated. However, absorption of the impurities in dialkyl sulfides may remove some contaminates but will not completely remove the variety of impurities due to the reversibility of the absorption process.

Some manufacturers of dimethyl sulfide and dimethyldisulfide have used odor-masking compounds to give the mixture a more pleasant odor (U.S. Pat. No. 5,559,271, U.S. Pat. No. 6,639,110). The compounds used have functional groups that are reactive with borane and therefore cannot be used in the application of DMSB preparation.

Removal of hydrogen sulfide, carbon disulfide, and thiols (collectively called acid gases) from gas streams and hydrocarbon mixtures has been tried with a number of methods, such as passing the gas through a packed bed calcinator (U.S. Pat. No. 6,136,144) or water and bromine (U.S. Pat. No. 5,433,828), absorption with nitrogen containing heterocycles (DE 19828977, U.S. Pat. No. 5,480,860) or reversible absorbents (U.S. Pat. No. 4,173,619, US 2005/0205470). Hydrocarbon purification to remove sulfurous and phosphine components prior to polymerization has used alkali metals on supports (U.S. Pat. No. 5,302,771, U.S. Pat. No. 6,124,410) or ion exchanged zeolites (U.S. Pat. No. 4,358,297). Other examples use amines on a solid support (U.S. Pat. No. 4,999,175), transition metal oxides (U.S. Pat. No. 5,157,201) or reaction with a Group 1B metal halide amine (U.S. Pat. No. 5,382,417).

Removal of alkyl sulfides and thiols in plant effluent by oxidation has been addressed (U.S. Pat. No. 6,015,536, U.S. Pat. No. 6,277,344, U.S. Pat. No. 5,439,641). Oxidation is not applicable to DMS purification because the DMS would also be oxidized.

High purity DMS is a desirable commercial product suitable as flavoring agent or solvent as well as low odor compounds made from it, i.e. DMSO or DMSB. Selective removal of undesirable components, while leaving the desired dimethyl sulfide, is not adequately addressed by current literature. Furthermore, oxidation methods are destructive to all components of the mixture. It is highly desirable to remove malodorous impurities from DMS while leaving the DMS unchanged.

It was therefore an object of the present invention to develop processes for the purification of dialkyl sulfides in order to provide low odor dialkyl sulfides, i.e. with an odor that is less noticeable compared to commercially available dialkyl sulfides.

SUMMARY OF THE INVENTION

Accordingly, new processes to purify dialkyl sulfides have been developed, comprising the step of bringing a dialkyl sulfide into contact with at least one base and/or at least one alkali or alkaline earth metal.

Moreover, low odor dialkyl sulfides have been developed that lack major malodorous impurities and methods of using these low odor dialkyl sulfides to prepare low odor products or as low odor solvent.

Furthermore, dialkyl sulfide borane complexes of high purity together with a process for their preparation have been developed and a improved process for enantioselective reductions employing these dialkyl sulfide borane complexes of high purity as reducing agent was found.

DETAILED DESCRIPTION OF THE INVENTION

One embodiment of the present invention is a process to purify dialkyl sulfides comprising the step of bringing a dialkyl sulfide into contact with at least one base and/or at least one alkali or alkaline earth metal, wherein the base is a metal alcoholate, a metal oxide, a metal or alkylammonium hydroxide, a metal or alkylammonium carbonate, a metal enolate, a metal amide or a metal hydride, wherein the metal is selected from the group, consisting of the alkali metals, the alkaline earth metals and the metals of the groups IIIa to VIIIa, Ib and IIb.

A preferred embodiment of the present invention is a process to purify dialkyl sulfides comprising the step of bringing a dialkyl sulfide into contact with at least one base and at least one alkali or alkaline earth metal.

According to the invention a dialkyl sulfide is a compound with the chemical formula R—S—R', wherein R and R' are independent from each other $C_1$-$C_{18}$ alkyl, $C_3$-$C_{14}$ cycloalkyl, substituted $C_1$-$C_{18}$ alkyl, substituted $C_3$-$C_{14}$ cycloalkyl or R and R' are connected as a divalent hydrocarbon moiety, that may contain further sulfur, oxygen, or nitrogen atoms, which together with the sulfur atom forms a cyclic dialkyl sulfide structure.

In a preferred embodiment of the present invention the dialkyl sulfide is dimethyl sulfide, diethyl sulfide, methyl ethyl sulfide, methyl isopropyl sulfide or thioxane.

As used in connection with the present invention, the term "$C_1$-$C_{18}$ alkyl" denotes a branched or an unbranched saturated hydrocarbon group comprising between 1 and 18 carbon atoms; examples are methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl and 1-2-pentylheptyl. Preferred are the alkyl groups methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl and octyl.

The term "$C_3$-$C_{14}$ cycloalkyl" denotes a saturated hydrocarbon group comprising between 3 and 14 carbon atoms including a mono- or polycyclic structural moiety. Examples are cyclopropyl, cyclobutyl, cyclopentyl, cyclohexyl, cycloheptyl, cyclooctyl, cyclononyl or cyclodecyl. Preferred are the cycloalkyl groups cyclopropyl, cyclopentyl and cyclohexyl.

The terms "substituted $C_1$-$C_{18}$ alkyl" or "substituted $C_3$-$C_{14}$ cycloalkyl" denotes an alkyl group or a cycloalkyl group as defined above in which at least one hydrogen atom is replaced by a fluorine atom.

Examples for cyclic dialkyl sulfides include thietane, thiolane, thioxane, 1,3-dithiane, 1,4-dithiane and 2-methyl-1,3-dithiane.

In a preferred embodiment of the present invention the dialkyl sulfide used as a starting material should have a purity of at least 95 wt.-%, preferably at least 99 wt.-%.

In another preferred embodiment of the present invention the dialkyl sulfide and the at least one base and/or at least one alkali or alkaline earth metal are brought into contact for a time in the range from about 1 second to about 24 hours, most preferred in the range between 1 minute and 3 hours.

In one embodiment of the present invention the dialkyl sulfides is brought into contact with at least one base, which is a metal alcoholate, a metal oxide, a metal or alkylammonium hydroxide, a metal or alkylammonium carbonate, a metal enolate, a metal amide or a metal hydride. The metal can be selected from the group, consisting of the alkali metals, the alkaline earth metals and the metals of the groups IIIa to VIIIa, Ib and IIb. Preferred are the alkali metals, magnesium, calcium, barium, scandium, titanium, vanadium, chromium, manganese, iron, cobalt, nickel, copper and zinc.

A metal alcoholate comprises at least one alkoxy group that can be derived from any branched or unbranched aliphatic alcohol. Examples of suitable metal alcoholates that can be employed in the present invention include potassium alcoholates, sodium alcoholates, lithium alcoholates, magnesium alcoholates, zinc alcoholates and titanium alcoholates derived from methanol, ethanol or t-butanol.

In another embodiment of the present invention the dialkyl sulfides is brought into contact with at least one alkali or alkaline earth metal. These metals can also be employed as mixtures with each other (i.e. as alloys) or with mercury (i.e. as amalgams). Preferred are dispersions of metals as well as metals on a supporting media such as alumina, silica, diatomaceous earth, graphite or other common mineral compositions. Most preferred is the use of alkali metals, especially of sodium-potassium alloys.

In cases where the metal employed does not only react with the impurities but also with the dialkyl sulfide to be purified a large excess of the metal should be avoided, otherwise the overall yield would be reduced.

In a preferred embodiment of the present invention the dialkyl sulfide is brought into contact with a metal alcoholate and optionally with at least one alkali or alkaline earth metal.

In one embodiment of the present invention the dialkyl sulfides is brought into contact with at least one base and with at least one alkali or alkaline earth metal consecutively in separate steps. In a preferred embodiment of the present invention the dialkyl sulfides is brought into contact with at least one base and with at least one alkali or alkaline earth metal simultaneously in one step.

In another preferred embodiment of the present invention the dialkyl sulfide is brought into contact with potassium tert.-butoxide and a sodium-potassium alloy.

Furthermore, the process of the present invention can be carried out in the liquid or in the gas phase. For a commercial process, the method of choice for high throughput would be to subject gaseous dialkyl sulfide to a fixed bed containing a metal and a base on a supporting media to allow for sufficient contact time in order to irreversible remove the malodorous components from the dialkyl sulfide.

By application of the processes disclosed in this invention to crude dialkyl sulfides essentially all of the malodorous impurities will be converted into non-volatile and perhaps insoluble derivatives. These derivatives can be removed from the dialkyl sulfide by any separation method known in the art. For example, precipitates of insoluble derivatives can be filtered. Reaction products with a considerable solubility in the dialkyl sulfide can be removed by distillation or extraction methods.

However, distillation of dialkyl sulfides can be problematic if carbon disulfide ($CS_2$) shall be removed. $CS_2$ forms an azeotrope with e.g. dimethyl sulfide (DMS), therefore distillation methods may not satisfactorily remove this contaminant. Reaction of carbon disulfide with a metal alcoholate generates a xanthate salt (Dunn, A. D.; Rudorf, W. Carbon Disulphide in Organic Chemistry; Ellis Horwood: Chichester 1989, p. 316), but this reaction is reversible under distillation conditions. Further reaction of the xanthate salt with an electrophile converts the salt to the xanthate ester which is stable and can easily be separated from the dialkyl sulfide by distillation. Since any thioate salt will also react with the electrophile to give the corresponding (and undesired) dialkyl sulfide, the electrophile should be chosen such that the products are non-volatile or high boiling.

Therefore, another embodiment of the present invention is a process to purify dialkyl sulfides comprising the steps of
  a) bringing a dialkyl sulfide into contact with at least one base and/or at least one alkali or alkaline earth metal, wherein the base is a metal alcoholate, a metal oxide, a metal or alkylammonium hydroxide, a metal or alkylammonium carbonate, a metal enolate, a metal amide or a metal hydride, wherein the metal is selected from the group, consisting of the alkali metals, the alkaline earth metals and the metals of the groups IIIa to VIIIa, Ib and IIb, and
  b) reacting the product of step a) with an electrophile, and
  c) distilling out the dialkyl sulfide.

In a preferred embodiment of the present invention the dialkyl sulfide is brought into contact in step a) with a metal alcoholate and optionally with at least one alkali or alkaline earth metal.

As electrophile any organic halide, methanesulfonate, trifluormethanesulfonate, p-toluenesulfonate and the like can be used. For the reason mentioned above, the organic residue of the electrophile should have a high molecular mass in order to generate high-boiling products. Examples of electrophiles suitable for the purification of low-boiling dialkyl sulfides include octyl bromide, benzyl bromide and benzyl chloride.

The new processes disclosed in this invention provide easy access to low odor dialkyl sulfides, which are of great value for the production of low odor compounds made from it, e.g. dimethyl sulfoxide or dimethyl sulfide borane complex from dimethyl sulfide.

Another embodiment of the present invention is the dialkyl sulfide obtainable by one of the processes disclosed above.

In the dialkyl sulfides according to the invention the content of each of the impurities carbon disulfide, methanethiol and dimethyldisulfide is below 0.01% wt. respectively.

Still another embodiment of the present invention is the method of using these low odor dialkyl sulfides to prepare low odor products or as a low odor solvent.

A preferred embodiment of the present invention is a method of using purified dialkyl sulfides to prepare dialkyl sulfide borane complexes of high purity. An even more preferred embodiment of the present invention is a method of using purified dimethyl sulfide to prepare dimethyl sulfide borane (DMSB) of high purity.

A further embodiment of the present invention is a process to prepare dialkyl sulfide borane complexes of high purity comprising the steps of
  a) bringing a dialkyl sulfide into contact with at least one base and/or at least one alkali or alkaline earth metal, wherein the base is a metal alcoholate, a metal oxide, a metal or alkylammonium hydroxide, a metal or alkylammonium carbonate, a metal enolate, a metal amide or a metal hydride, wherein the metal is selected from the group, consisting of the alkali metals, the alkaline earth metals and the metals of the groups IIIa to VIIIa, Ib and IIb of the periodic table of elements, and
  b) optionally reacting the product of step a) with an electrophile and distilling out the dialkyl sulfide, and
  c) reacting the dialkyl sulfide purified according to step a) and optionally step b) with diborane.

A preferred embodiment of the present invention is a process to prepare dimethyl sulfide borane (DMSB) of high purity by the process described above wherein dimethyl sulfide is employed as dialkyl sulfide.

The reaction of purified dialkyl sulfide with diborane according to step c) of the process described above is usually carried out at temperatures between −10 and +50° C., preferably at ambient temperature. Diborane is preferably employed in gaseous form and the reaction is preferably carried out in a pressurized vessel.

Another embodiment of the present invention is the dialkyl sulfide borane complex of high purity obtainable by the process disclosed above.

In the dialkyl sulfide borane complexes according to the invention the content of each of the impurities carbon disulfide, methanethiol and dimethyldisulfide is below 0.01% wt. respectively.

It was found that the enantiomeric excess obtained in enantioselective reductions with dialkyl sulfide boranes as reducing agent is higher with dialkyl sulfide borane complexes of high purity according to the invention compared with regular dialkyl sulfide borane complexes. This improvement is due to the lack of impurities like dimethyldisulfide (DMDS) or alkyl thiols (as shown by addition experiments, cf. Example 3) that are effectively removed by the purification processes disclosed above.

Since for pharmaceutical products an enantiomeric excess of at least 99.5% is required by regulations (Carey, J. S.; Laffan, D.; Thomson, C.; Williams, M. T. Organic & Biomolecular Chemistry 2006, 4, 2337), application of the dialkyl sulfide borane complexes of high purity according to the invention is very advantageous because it helps to avoid purification steps.

Therefore, another embodiment of the present invention is a process for enantioselective reductions which comprises using as reducing agent a dialkyl sulfide borane complex of high purity according to the invention.

Enantioselective reductions with dialkyl sulfide boranes as reducing agent are usually carried out in the presence of chiral boron-containing catalysts like tetrahydro-1-methyl-3,3-diphenyl-1H,3H-pyrrolo[1,2-c][1,3,2]oxazaborole (known as the (R)- or (S)-MeCBS oxazaborolidine reagent, see Corey, E. J.; Helal, C. J. Angew. Chem. Int. Ed. 1998, 37, 1986) or chiral spiroborates like (R)- or (S)-2-[(1,3,2-dioxaborolan-2-yloxy)diphenylmethyl]pyrrolidine (see Ortiz, M. M.; Stepanenko, V.; Correa, W.; Jesus, M. D.; Sandraliz, E.; Ortiz, L. Tetrahedron Asymmetry 2006, 17, 122).

In a preferred embodiment of the present invention the enantioselective reduction is the reduction of a prochiral ketone or imine.

The following examples illustrate the present invention without limitation of the same.

EXAMPLES

Example 1

To see the affect of various treatments with alkali metals and/or bases on the odor of commercial dimethyl sulfide a series of experiments were completed. Impure dimethyl sulfide (about 99.0% DMS, Chevron-Phillips) was stirred with various reagents for 1 hour at ambient temperature in the liquid phase. Based on odor detection by (4) human volunteers, the odor after contact with the reagents was determined and related to a particular known odor.

TABLE 1

Odor assessment for dimethyl sulfide after different treatments

| Entry # | Treatment | Odor |
|---|---|---|
| 1 | No treatment | Strong unpleasant odor |
| 2 | Sodium hydroxide | Lower odor but still rotten cabbage |
| 3 | Potassium tert.-butoxide (KTB) | Lower odor but still rotten cabbage |
| 4 | NaK | Strong $CS_2$ odor (described as pine) |
| 5 | NaK and KTB/filtered | Boiled sweet corn odor |
| 6 | NaK and KTB/distilled | Trace odor of $CS_2$, pine |
| 7 | NaK and OctBr/distilled | Only odor of sweet corn |
| 8 | NaK and BnBr/distilled | Slight musty odor |
| 9 | NaK and BnCl/distilled | Only odor of sweet corn |
| 10 | NaK, KTB and OctBr/distilled | Boiled sweet corn odor |

The addition of sodium hydroxide (NaOH, entry 2, 1 g/10 ml DMS) or potassium tert.-butoxide (KTB, entry 3, 1 g/10 ml DMS) to DMS caused a noticeable warming of the solution due primarily to the base dissolving. The residual odor of base treated samples was of rotten cabbage due to dimethyldisulfide impurities remaining in the DMS. Addition of liquid sodium-potassium-alloy (NaK, entry 4, 0.2 g/10 ml DMS) showed visible signs of reaction by gas evolution (hydrogen) and a tan solid formed on the beads of NaK. The odor after NaK treatment was still strongly of carbon disulfide. KTB was added to NaK treated DMS (entry 5, 1 g KTB+0.2 g NaK/10 ml DMS) which greatly improved the odor. The odor of this filtered sample was of boiled sweet corn.

The NaK and KTB treated sample was distilled from the solids and remaining unreacted NaK. The DMS distillate (entry 6) still had a slight odor of carbon disulfide. Distillation of the DMS overcomes the problem of dissolved basic compounds, however due to the reversible nature of the reaction of carbon disulfide and base, the odor of distilled DMS had a hint of $CS_2$ odor. To adequately remove the traces of carbon disulfide an electrophile (bromooctane, benzyl bromide, benzyl chloride) was added after the addition of alkali metal and/or base to form the xanthate ester and potassium bromide. After distillation the DMS produced by this method also had an odor of corn (entries 7, 9 and 10, amounts of reagents are listed in example 2).

The most satisfactory odor removal was by contacting DMS with a combination of NaK and KTB.

Example 2

The following experimental procedure was used for DMS from two different sources of dimethyl sulfide, Chevron-Phillips and Gaylord. DMS (100 g) was weighed into an oven dried round-bottom flask. NaK (0.5 g, 72 wt % K) was added to the sample and stirring commenced at room temperature for 1 h. One of three alkylating agents (1.96 g benzyl chloride, 2.65 g benzyl bromide or 2.99 g 1-bromooctane) was then added. In each sample some solid precipitate formed. The dimethyl sulfide was distilled from the solids at a boiling range of 36-37.5° C. The distilled samples were then analyzed by GC/MS for purity, see Table 2 for results.

TABLE 2

Analytical data (GC/MS) for dimethyl sulfides after different treatments.

| Entry # | Treatment | Chevron-Phillips | Gaylord |
|---|---|---|---|
| 1 | No treatment | 99.077 DMS | 99.751 DMS |
|  |  | 0.32 CS2 | 0.018 MeSH |
|  |  | 0.024 MeSH | 0.036 EtSMe |
|  |  | 0.259 DMDS | 0.19 acetone |
| 2 | NaK and OctBr/distilled | 99.829 DMS | 99.885 DMS |
|  |  | 0.00 $CS_2$ | 0.00 MeSH |
|  |  | 0.00 MeSH | 0.017 EtSMe |
|  |  | 0.00 DMDS | 0.02 acetone |
|  |  |  | 0.019 octane |
|  |  |  | 0.018 OctBr |
| 3 | NaK and BnBr/distilled | 99.76 DMS | 99.889 DMS |
|  |  | 0.00 $CS_2$ | 0.00 MeSH |
|  |  | 0.00 MeSH | 0.018 EtSMe |
|  |  | 0.001 DMDS | 0.079 acetone |
| 4 | NaK and BnCl/distilled | 99.077 DMS | 99.922 DMS |
|  |  | 0.00 $CS_2$ | 0.00 MeSH |
|  |  | 0.00 MeSH | 0.018 EtSMe |
|  |  | 0.002 DMDS | 0.042 acetone |

All figures are % wt..
DMS is dimethyl sulfide,
$CS_2$ is carbon disulfide,
DMDS is dimethyldisulfide,
MeSH is methanethiol,
EtSMe is ethyl methyl sulfide,
OctBr is 1-bromooctane,
BnCl is benzyl chloride and BnBr is benzyl bromide.
Traces of acetone were from cleaning of the syringe between samples Example 3

The following experimental procedure was used for the enantioselective reduction of acetophenone with DMSB of different purity in the presence of a chiral catalyst:

High purity DMSB was prepared as a 10M solution by addition of gaseous diborane at ambient temperature to DMS that has been purified according to the procedure disclosed in Table 2, Entry #4.

3.3 ml of a stock solution of the respective sulfide impurity in toluene (0.02 eq. impurity vs. acetophenone) were mixed with the high purity DMSB (6.24 mmol, 592 μl of the 10M DMSB solution, 0.75 eq. vs. acetophenone), the mixture was stirred at ambient temperatures for 60 minutes, and then the chiral catalyst ((R)-MeCBS ((R)-tetrahydro-1-methyl-3,3-diphenyl-1H,3H-pyrrolo[1,2-c][1,3,2]oxazaborole): 167 μl, 0.167 mmol, 1M solution in toluene, 0.02 eq.; or (R)-DPP Spiro ((R)-2-[(1,3,2-dioxaborolan-2-yloxy)diphenylmethyl] pyrrolidine): 53.81 mg, 0.167 mmol, 0.02 eq.) was added. The mixture was agitated for 5 minutes before a solution of acetophenone in toluene (834.5 mg, 8.32 mmol in 3.2 ml toluene to result in 1M acetophenone solution during reaction, 1 eq.) was added using a syringe pump within 10 minutes. Five minutes after the addition was completed, 0.3 ml of a sample was taken and hydrolyzed in 2M hydrogen chloride (2 ml). The top layer was diluted with toluene and investigated further by GC analysis for conversion and enantioselectivity. The reaction was repeated using DMSB prepared with DMS from conventional raw material sources such as from Chevron-Phillips or Gaylord and the enantioselectivity was compared.

TABLE 3

Results for the enantioselective reduction of acetophenone
with DMSB of different purity in the presence of a chiral catalyst.

| Entry # | Catalyst | Impurity added | DMSB Quality | Conversion (%) | ee (%) |
|---|---|---|---|---|---|
| 1 | (R)—MeCBS | — | Chevron-Phillips | 99.86 | 97.6 |
| 2 | (R)—MeCBS | — | Gaylord | 99.74 | 98.12 |
| 3 | (R)—MeCBS | — | High purity | 99.6 | 99.04 |
| 4 | (R)—MeCBS | DMDS | High purity | 99.4 | 98.16 |
| 5 | (R)—MeCBS | EtSH | High purity | 99.86 | 94.67 |
| 6 | (R)—DPP Spiro | — | High purity | 99.9 | 99.02 |
| 7 | (R)—DPP Spiro | DMDS | High purity | 99.9 | 98.14 |
| 8 | (R)—DPP Spiro | EtSH | High purity | 99.8 | 96.46 |

DMSB is dimethyl sulfide borane,
DMDS is dimethyldisulfide,
EtSH is ethanethiol,
(R)—MeCBS is (R)-tetrahydro-1-methyl-3,3-diphenyl-1H,3H-pyrrolo[1,2-c][1,3,2]oxazaborole,
(R)—DPP Spiro is (R)-2-[(1,3,2-dioxaborolan-2-yloxy)diphenylmethyl]pyrrolidine All the references described above are incorporated by reference in its entirety for all useful purposes.

While there are shown and described certain specific structures embodying the invention, it will be manifest to those skilled in the art that various modifications and rearrangements of the parts may be made without departing from the spirit and scope of the underlying inventive concept and the same is not limited to the particular forms herein shown and described.

The invention claimed is:

1. A process to prepare a dialkyl sulfide borane complex comprising the steps of
   a) bringing a dialkyl sulfide into contact with at least one base and/or at least one alkali or alkaline earth metal, wherein the base is a metal alcoholate, a metal oxide, a metal hydroxide, alkylammonium hydroxide, a metal or alkylammonium carbonate, a metal enolate, a metal amide or a metal hydride, wherein the metal is selected from the group, consisting of the alkali metals, the alkaline earth metals and the metals of the groups IIIa to VIIIa, Ib and IIb of the periodic table of elements, and
   b) reacting the product of step a) with an alkyl or benzyl halide,
   c) distilling out the dialkyl sulfide, and
   d) reacting the dialkyl sulfide purified according to steps a) to c) with diborane.

2. The process according to claim 1, wherein the dialkyl sulfide is dimethyl sulfide.

3. A process for enantioselective reductions which comprises using as reducing agent the dialkyl sulfide borane complex obtained by a process by the process according to claim 1.

4. The process according to claim 3, wherein the enantioselective reduction is the reduction of a prochiral ketone or imine.

5. The process according to claim 3, wherein the enantioselective reduction is carried out in the presence of a tetrahydro-1-methyl-3,3-diphenyl-1H,3H-pyrrolo[1,2-c][1,3,2]oxazaborole or a 2-[(1,3,2-dioxaborolan-2-yloxy)diphenylmethyl]pyrrolidine as a catalyst.

6. The process according to claim 4, wherein the enantioselective reduction is carried out in the presence of a tetrahydro-1-methyl-3,3-diphenyl-1H,3H-pyrrolo[1,2-c][1,3,2]oxazaborole or a 2-[(1,3,2-dioxaborolan-2-yloxy)diphenylmethyl]pyrrolidine as a catalyst.

7. The process according to claim 1, wherein the step d) is carried out at a temperature from −10 to 50° C. and the diborane is in gaseous form.

8. The process according to claim 7, wherein the step d) is carried out at ambient temperature.

9. The process according to claim 1, wherein the dialkyl sulfide borane has a content of each of the impurities carbon disulfide, methanethiol and dimethyldisulfide below 0.01 wt. % respectively.

* * * * *